US005119830A

United States Patent [19]

Davis

[11] Patent Number: 5,119,830

[45] Date of Patent: Jun. 9, 1992

[54] ANALYTICAL SPECIMEN CUP WITH TESTING MEANS

[75] Inventor: Richard C. Davis, Palm Harbor, Fla.

[73] Assignee: Code Blue Medical Corporation, Clearwater, Fla.

[21] Appl. No.: 680,079

[22] Filed: Apr. 3, 1991

[51] Int. Cl.[5] ........ A61B 5/00

[52] U.S. Cl. ........ 128/771; 604/404

[58] Field of Search ........ 128/760, 771; 604/317, 604/318, 403, 404

[56] References Cited

U.S. PATENT DOCUMENTS

| | | | |
|---|---|---|---|
| 3,774,455 | 11/1973 | Seidler et al. | 73/444 |
| 3,924,741 | 12/1975 | Kachur et al. | 206/221 |
| 4,024,952 | 5/1977 | Leitz | 206/221 |
| 4,109,530 | 8/1978 | Kim | 73/427 |
| 4,827,944 | 5/1989 | Nugent | 128/771 |

*Primary Examiner*—Max Hindenburg
*Attorney, Agent, or Firm*—Griffin Branigan & Butler

[57] ABSTRACT

An analytical specimen cup (10) has outer and inner partitions (26, 34) in a lid (14) thereof, with the outer partition being flexible and transparent and the inner partition having a valve (46) comprised of a frangible portion (50) of the inner partition. A chemical test strip (24) is mounted in a test space (42) between the outer and inner partitions and a fluid specimen in the cup can be introduced to the chemical test strip in the test space by manipulating the frangible valve (46) to break it open via the flexible outer partition. The inner partition is formed as a one-piece lid main member (22) with most of the rest of the lid whereas the outer partition is mounted to cover an indentation (30) into a top surface of the lid main member to define the test space in the indentation.

18 Claims, 4 Drawing Sheets

ANALYTICAL SPECIMEN CUP WITH TESTING MEANS

BACKGROUND OF THE INVENTION

This invention relates generally to the art of handling and testing fluid specimens and more particularly to a cup which can be used to receive, transport and store a fluid specimen as well as to provide indications of characteristics of the fluid specimen.

Fluid specimens, particularly body fluids such as blood, spinal fluid and urine, are normally collected and stored in containers, vials or cups, with some having sealable lids. When it is desired to run tests on liquid, or fluid specimens contained in the cups, the lids thereof are normally punctured or removed and specimen samples are taken out of the cups and transferred to test apparatus. A difficulty with prior-art cups is that when the lids thereof are removed or punctured specimen samples may become contaminated or fluid can easily escape from the cups and thereby contaminate an operator as well as surrounding equipment. Furthermore, with the caps removed, spillage and loss of entire specimens commonly occurs. Thus, it is an object of this invention to provide a specimen cup for collecting, transporting and storing a fluid specimen with which tests on the contained fluid specimen can be run without removing a lid thereof.

At least one body fluid sample collection tube has been suggested by Nugent in U.S. Pat. No. 4,827,944 in which a tube has a plurality of bores for allowing passage of a sample in the tube to impregnate adjacent dry chemistry patches. A plastic film wrap is pre-shrunk over the tube and the patches so as not to allow specimen fluids to escape beyond the patches. When a specimen is introduced into the collection tube of this invention a portion of the specimen passes immediately through the bores and impregnates simultaneously and immediately the plurality of patches so that an indication can be made immediately of a suspected condition or conditions for which the testing is taking place. A difficulty with this system is that it is usually not desirable to immediately test collected body fluids when they are first placed in a specimen cup. In this regard, some chemical patches, pads or test strips are time sensitive and do not, therefore, retain appropriate test colors over long periods of time. Thus, it is an object of this invention to provide such a sealed analytical specimen cup wherein chemical test strips can be selectively activated with a fluid specimen contained therein only when a user desires such activation.

In the past, dry chemical test strips have been introduced into urine samples or specimens by dropping them therein. Such a procedure often contaminates a fluid specimen itself, thereby adversely affecting further tests run on the fluid specimen. Thus, it is an object of this invention to provide an analytical specimen cup with which a chemical test strip can be introduced into a fluid specimen without fear of contaminating the fluid specimen.

Similarly, such chemical test strips have been developed to provide visual indications of quantitative properties of a specimen fluid such as: pH, protein, glucose, ketone, bilirubin, blood, urobilinogen, and many other body fluid components. Changes in color of a chemical test strip are indicative of these characteristics of fluid specimens and therefore provide a user with information as to what, if any, further testing may be required.

Usually, an operator, user, or other person collecting a fluid specimen is not someone who will "read" or analyze an initial chemical test strip to determine what, if any, further tests are necessary. However, if a chemical test strip has been exposed too long to a fluid specimen, it is sometimes difficult for a user, or operator, to accurately read the test strip thereby making determinations for further tests impossible. Thus, it is an object of this invention to provide an analytical specimen cup including a chemical test strip which is selectively exposed to a fluid specimen contained in the cup only upon demand by an appropriate user.

SUMMARY OF THE INVENTION

According to principles of this invention, an analytical specimen cup includes inner and outer partitions for forming a test space with the inner partition including a valve which can be selectively operated from outside the specimen cup and the outer partition being transparent so that a chemical test strip located in the test space can be viewed from outside the specimen cup. The outer partition also provides a complete seal of the test space. In a preferred embodiment, the outer partition is flexible and the valve is a frangible portion of the inner partition. The frangible valve is broken open by manipulation via the flexible outer partition which flexes to allow such manipulation. The outer and inner partitions are mounted on a lid with the inner partition being part of a lid main member and the outer partition covering and sealing an indentation in the lid main member.

BRIEF DESCRIPTION OF THE DRAWINGS

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

DETAILED DESCRIPTION OF A PREFERRED EMBODIMENT

Figure 1:
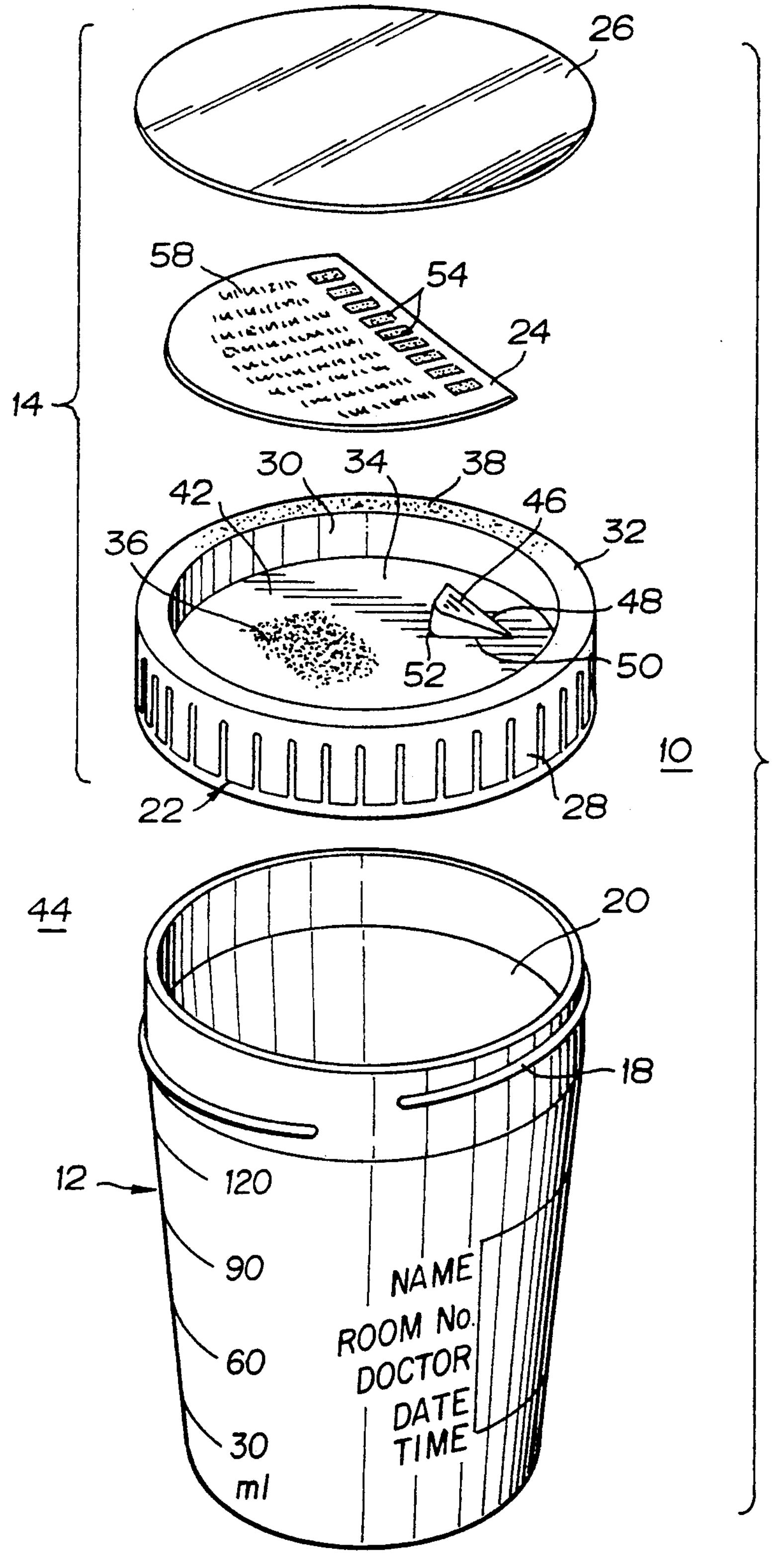
FIG. 1 is an isometric exploded view of an analytical specimen cup of this invention.
Figure 2:
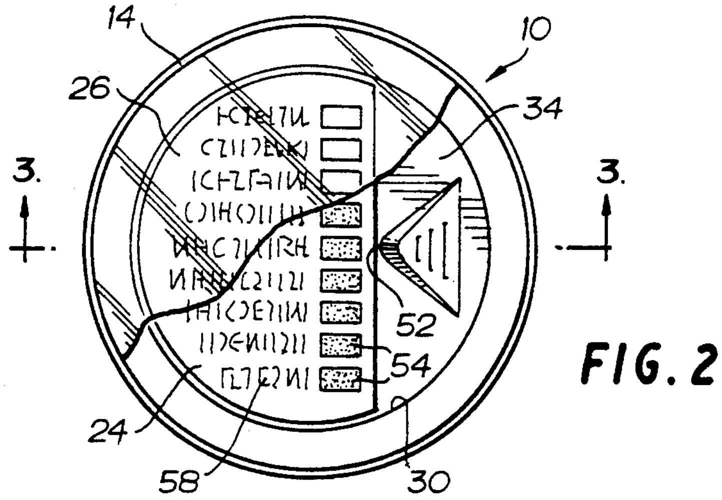
FIG. 2 is a top view of the analytical specimen cup of FIG. 1.
Figure 4:
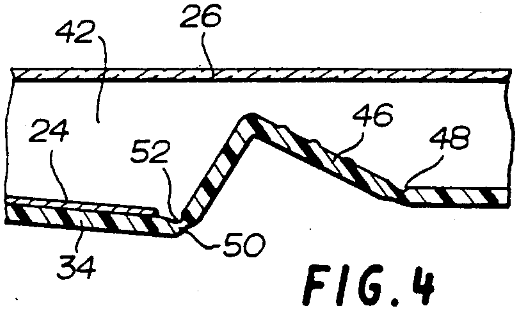
FIG. 4 is an enlarged sectional view similar to FIG. 3 of a segment of the lid being in a deactivated configuration.

An analytical specimen cup 10 of this invention includes a base container 12 and a lid 14. The analytical specimen cup 10 is for collecting and sealingly enclosing a fluid specimen within a container wall thereof. The base container 12 forms a lower part of the container wall and the lid 14 forms an upper part of the container wall, with the lid 14 having threads 16 which mesh with threads 18 of the base container 12 to sealingly hold the lid 14 on the base container 12 so that the container wall defines a container cavity 20 in which the fluid specimen is collected, transported and/or stored. The container wall, including the base container 12 and the lid 14 is constructed of a material which is normally impervious to fluid specimens contained therein. The lid 14 is comprised of a lid main member 22 having a dry chemical test strip 24 and a transparent, circular, thin, sheet of mylar 26 adhered thereto. In this respect, the lid main member 22 has the threads 16 on an inner surface of a skirt 28 thereof and includes an indentation 30 in a top surface thereof surrounded by a rim 32 above the skirt 28. A floor 34 of the main member 22 defines the indentation 30. The floor 34 is sloped slightly downwardly, in a conical manner, so that any fluid contained within the test space will readily drain back into the container through a valve shell 46 when the container is upright. The chemical test strip 24 is adhered by an adhesive 36 or otherwise bonded or welded to the floor 34 and the sheet of mylar 26 is adhered about its outer perimeter edge by an adhesive 38 or otherwise sealably bonded or welded to the rim 32 of the lid main member 22. The floor 34, the sheet of mylar 26, and an indentation wall 40 define a test space 42 in which the chemical test strip 24 is located. The sheet of mylar 26 is attached to the rim 32 in such a manner that fluid contained in the test space 42 cannot escape to outside atmosphere 44 neither can atmospheric contaminants enter into the test space.

Figure 3:
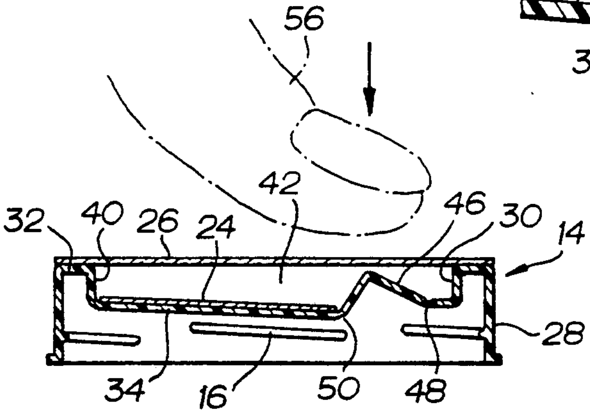
FIG. 3 is a side sectional view taken on line 3—3 in FIG. 2 with a finger of an operator or user shown therein for selectively activating a chemical test strip of a lid.
Figure 5:
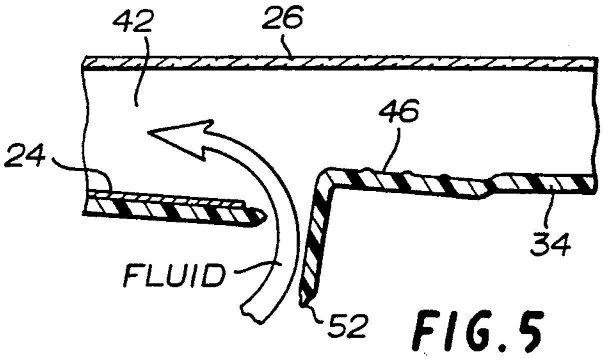
FIG. 5 is a sectional view similar to FIG. 4, but with the segment of the lid being in an activated configuration.

The floor 34 is generally almost flat with a slight conical slope but further includes an integral, upwardly-protruding, wedge-shaped shell, or valve, 46 which is attached to the rest of the floor 34 at an integral hinge 48 and an integral frangible connection 50. In this respect, when one presses downwardly on an apex of the wedge-shaped shell 46, as is shown in FIG. 3, most pressure is initially applied at an apical aspect of a connection point 52 of the shell 46 with the rest of the floor 34 so that this point breaks away from the rest of the floor 34 thereby allowing more pressure to be exerted at connection points between the shell 46 and the rest of the floor 34 at two positions which progressively move toward the hinge 48 as the shell moves downwardly and progressively breaks away from the floor 34 at these two moving points. This is shown in FIG. 5.

The chemical test strip 24 includes pads 54 thereon, each of which is for determining a characteristic of a fluid specimen by changing color upon contact with the fluid specimen.

The sheet of mylar 26 is highly flexible and somewhat resilient so that it can be flexed downwardly when pressed by a finger 56, as shown in FIG. 3, which is being used to break the shell 46 away from the rest of the floor 34. In this regard, although the sheet of mylar 26 flexes to allow manipulation of the shell 46, it does not break nor does it break away from the rim 32 of the lid main member 22, but rather remains sealed.

Describing next operation of the analytical specimen cup 10, the lid 14 is removed from the base container 12 and a specimen, such as a urine specimen, is deposited into the base container 12. The lid 14 is then screwed back on the base container 12. In this configuration, the analytic specimen cup, with the enclosed urine specimen, can be stored and/or transported, to a laboratory for example, without fear that the urine specimen will prematurely come into contact with the chemical test strip pads 54 because the lid main member 22 of the lid is totally sealed with the frangible connection 50 and the hinge 48 being thinner than the rest of the lid main member 22, but not having perforations and not allowing passage of fluids, such as the urine specimen. However, once an operator, such as a laboratory technician is ready to get a preliminary indication, or reading, of characteristics of the fluid specimen in the analytical specimen cup 10, he or she presses downwardly with his or her finger 56 against an upper surface of the transparent sheet of mylar and urges it downwardly against an upper surface of the shell 46 of the lid main member so as to break the frangible connection 50 at the apical connection point 52 thereof and with continued pressure, along sides thereof. This causes the shell 46 to downwardly rotate about the hinge 48 into the base container 12 as depicted in FIG. 5. In this configuration, the urine specimen can now enter the test space 42 between an outer partition (the transparent sheet 26), an inner partition (the floor 34), and the indentation wall 40 so as to come into contact with the chemical test strip pads 54. When urine contacts the chemical test strip pads 54 the characteristics thereof, in conjunction with chemicals in the chemical test strip pads 54, cause the chemical test strip pads to change color, thereby providing visual indications to the operator in accordance with the precalibrated indicator markings 68 beside the respective chemical test strip pads 54 corresponding to such characteristics. These changes in colors can be easily read by the operator through the transparent sheet 26.

It will be appreciated by those of ordinary skill in the art that the analytical specimen cup of this invention allows collection and transportation of a fluid specimen in the same manner as have specimen cups in the past, while also allowing an operator to selectively get an accurate preliminary reading with chemical test strip pads of characteristics of the specimen without exposing it to outside atmosphere, or having to come into direct contact with the specimen himself, thereby producing the possibility of contaminating him- or herself or surrounding equipment with the fluid specimen contained in the analytical specimen cup, or possibly spilling and losing the entire specimen itself.

It is beneficial that a selectively operatable valve is included, such as the shell 46 which is attached to the rest of the lid main member by means of a hinge portion and a frangible-connection portion. In this respect, the lid main member, including the shell 46 and its hinge and frangible connection are all molded as one piece, preferably of a resinous plastic, with the frangible connection 50 and the hinge 48 being appropriately thinner than the rest of the lid main member.

It is also beneficial to construct the transparent sheet of a separate member which is adhered, or otherwise sealably attached, to the lid main member covering an indentation thereinto.

Also, operation of the valve, that is, the shell 46, through a flexible transparent sheet member provides a structure which is extremely easy to manufacture and use. In this respect, it is also convenient for the transparent sheet to be resilient, as is the transparent sheet 26, so that it can be retained in a tight, flat arrangement for looking through but yet hand manipulations can be transmitted therethrough to manipulate the shell, or valve. In this regard, the transparent sheet stretches downwardly with downward pressure of a finger for manipulating the shell 46 but springs back to its tight configuration once the manipulations have been accomplished. It would also be possible, however, to use a sealably attached loose transparent sheet rather than a tight resilient one.

Although the hand actuatable valve described herein, is, in a preferred embodiment, mounted in the lid, it would also be possible to mount such a hand-actuatable valve in the base or sidewall of the container, although it is thought that such an arrangement would not be as convenient to manufacture and use, and would be more prone to accidental activation.

In this regard, it is beneficial that the hand actuatable valve, or shell, is mounted in an indentation of a main lid member with a transparent sheet covering the indentation because such an arrangement protects the valve from inadvertent actuation and also provides a normally relatively smooth outer contour of the analytical specimen cup for stacking or otherwise handling.

Further, it is beneficial that the floor 34 is sloped toward the apical connection point 52 in a conical manner so that fluid specimen contained in the test space 42 easily runs back into the container cavity 20 when the analytical specimen cup 10 is in an upright attitude.

Looking at a second, preferred, embodiment of the invention, which is shown in FIGS. 6–9, the base container 12 is the same as in the first embodiment of FIG. 1. However a lid main member 22′ of a lid 14′ is generally rectangular in shape rather than being round as is the lid 14 of the FIG. 1 embodiment. Also, an indentation 30′ defined in the top of the lid main member 22′ has a transparent sheet step 66 and a protective-cover step 68 for respectively receiving a rectangular transparent sheet of mylar 26′ and a rectangular opaque protective-cover foil 70. Since the indentation 30′ is rectangular in shape, its floor 34′ is also rectangular in shape so that a chem strip 24′, which is held to the floor 34′ by adhesive 36′, can also be rectangular in shape providing more room for necessary indicia 58′.

The opaque protective-cover foil 70 provides several extremely important functions. Firstly, chem pads 54′ are usually light sensitive so that their effectiveness deteriorates when they are exposed to light for an extended period of time. Thus, the opaque protective-cover foil 70, in combination with the opaque lid main member 22′, prevents light from reaching the chem pads 54′ and therefore protects the effectiveness of these chem pads 54′. Also, the protective-cover foil 70 prevents a user from inadvertently damaging the transparent sheet of mylar 26′ and/or from pressing on a shell 46 and thereby breaking a frangible connection point 52 as was described for operation of FIG. 1. In this regard, the protective-cover foil 70 is made of a rather thick material which can be torn completely or partially away using a tab 72 thereof when it is desired to activate the shell valve 46, as was previously described for the FIG. 1 embodiment, to make a preliminary analysis of liquid contained in the base container 12. Once the protective-cover foil 70 is removed, an operator can press on the shell 46 through the transparent sheet of mylar 26′, as is similarly depicted in FIG. 3, to activate the chem pads 54.

Although the protective-cover foil 70 could be a metallic foil, it could also be a hard cardboard sheet or other appropriate-material shield.

Figure 6:
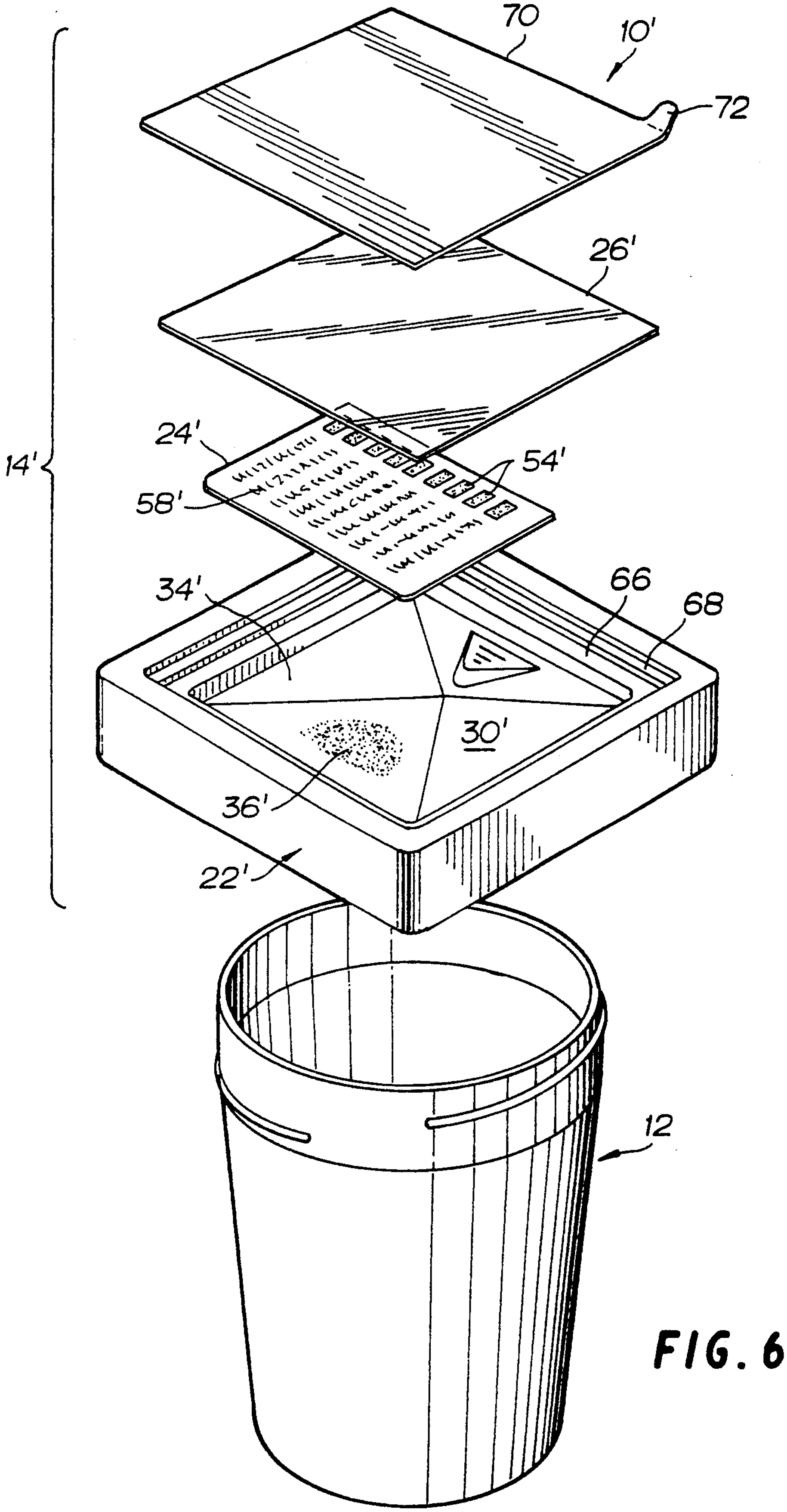
FIG. 6 is an isometric exploded view of a second-embodiment analytical specimen cup of this invention.
Figure 7:
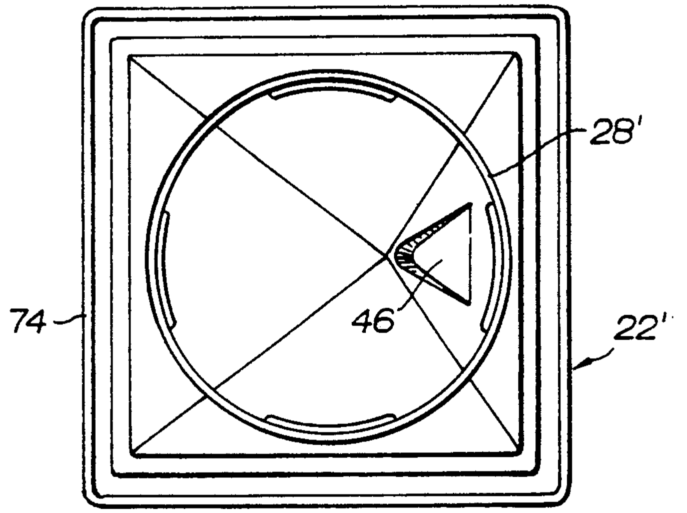
FIG. 7 is a bottom plan view of an assembled lid of the second embodiment of FIG. 6.
Figure 8:
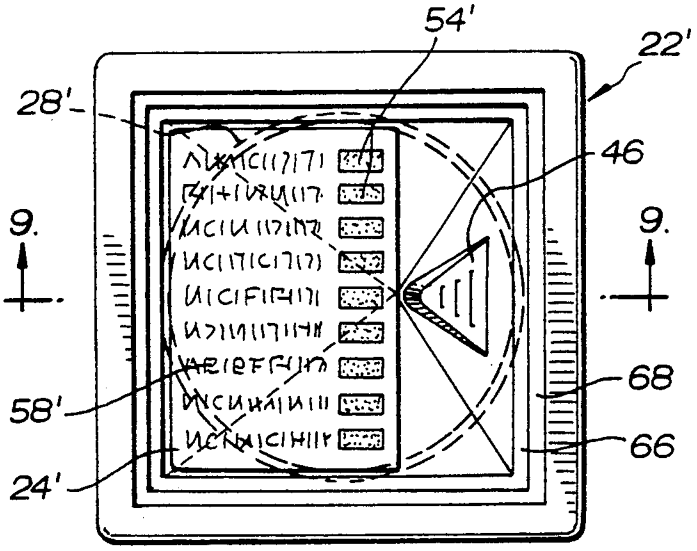
FIG. 8 is a top plan view of the lid of FIG. 7 without a protective-cover foil.
Figure 9:
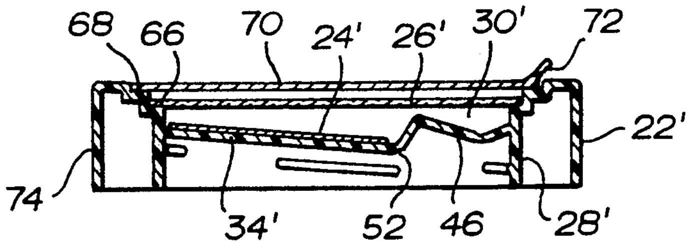
FIG. 9 is a cross sectional view taken on line 9—9 in FIG. 8, but with the protective-cover foil.

In the FIG. 6 embodiment, the lid 14′ still includes a round screw-on skirt 28′ for screwing onto the base container 12. However, it also includes a further outer skirt 74. Many configurations combining all or part of these elements other than those depicted in the drawings are also possible.

Although the invention has been described relative to preferred embodiments, it will be understood by those of ordinary skill in the art that various changes in structure and operation can be made therein within the scope of the invention.

The embodiments of the invention in which an exclusive property or privilege are claimed or defined are as follows:

1. An analytical specimen cup for testing fluid specimen contained therein, said cup comprising a container wall enclosing said fluid specimen in a container cavity defined by said container wall, an area of said container wall including normally fluid-impervious outer and inner partitions forming a test space therebetween, said inner partition being between said container cavity and said test space and said outer partition being between said test space and outside atmosphere, said container further including a testing-strip means mounted in said test space for contacting said fluid specimen in said test space and changing its appearance in response thereto so as to provide a visual indication of a characteristic of said fluid specimen, said outer partition being at least partially transparent so that said test strip can be viewed from outside atmosphere therethrough, said inner partition including a selectively-operated valve means for being initially closed but being selectively opened from outside atmosphere to allow fluid specimen to enter said test space from said container cavity while not allowing said fluid specimen to escape from said container cavity to outside atmosphere;

whereby a fluid specimen can be placed into said container cavity without contacting said test-strip means, but can be allowed access to contact said test-strip means by a person in outside atmosphere for activating said test-strip means to provide an indication of a characteristic of said fluid specimen to said person in outside atmosphere without allowing said fluid sample to escape to outside atmosphere.

2. An analytical specimen cup as in claim 1 wherein said inner and outer partitions are mounted on a removable lid forming the specimen cup.

3. An analytical specimen cup as in claim 2 wherein the outer partition is constructed of a separate piece which is attached to a lid main member, and the inner partition and most of a rest of the lid are constructed of one piece to form the lid main member.

4. An analytical specimen cup as in claim 3 wherein said valve means includes a frangible portion of said lid main member.

5. An analytical specimen cup as in claim 4 wherein said outer partition is flexible and flexes to allow manipulation of said frangible portion to break said frangible portion from the rest of said lid main member through said outer partition.

6. An analytical specimen cup as in claim 5 wherein is further included an opaque, at least partially removable, protective cover mounted on said lid covering said outer partition for protecting said outer partition.

7. An analytical specimen cup as in claim 2 wherein said lid has an indentation therein in which said valve means is located and wherein said outer partition covers said indentation.

8. An analytical specimen cup as in claim 2 wherein is further included an opaque, at least partially removable, protective cover mounted on said container wall covering said outer partition for protecting said outer partition.

9. An analytical specimen cup as in claim 2 wherein said removable lid is rectangular in configuration while the remainder of said specimen cup in round.

10. An analytical specimen cup as in claim 9 wherein is further included an opaque, at least partially removable, protective cover mounted on said lid covering said outer partition for protecting said outer partition.

11. An analytical specimen cup as in claim 1 wherein said valve means is a frangible portion of said analytical cup positioned on said inner partition.

12. An analytical specimen cup as in claim 11 wherein said outer partition is flexible and flexes to allow said frangible portion to be manipulated and broken therethrough.

13. An analytical specimen cup as in claim 12 wherein is further included an opaque, at least partially removable, protective cover mounted on said container wall covering said outer partition for protecting said outer partition.

14. An analytical specimen cup as in claim 1 wherein said valve means is located on said inner partition and said inner partition is mounted in an indentation of said analytical specimen cup, with said outer partition covering said indentation.

15. An analytical specimen cup as in claim 1 wherein said outer partition is flexible and flexes to allow said valve means to be manipulated therethrough.

16. An analytical specimen cup as in claim 15 wherein is further included an opaque, at least partially removable, protective cover mounted on said container wall covering said outer partition for protecting said outer partition.

17. An analytical specimen cup as in claim 1 wherein said inner partition is approximately horizontal when said specimen cup is in an upright attitude but has a slightly funnelled shape so that any excess fluid specimen readily drains back into the specimen container through the valve means when the container is upright.

18. An analytical specimen cup as in claim 1 wherein is further included an opaque, at least partially removable, protective cover mounted on said container wall covering said outer partition for protecting said outer partition.

* * * * *